United States Patent [19]

Ayers et al.

[11] 4,246,258

[45] Jan. 20, 1981

[54] BIOLOGICAL CONTROL SYSTEM

[75] Inventors: William A. Ayers; Peter B. Adams, both of Beltsville, Md.

[73] Assignee: The United States of America as represented by the Secretary of Agriculture, Washington, D.C.

[21] Appl. No.: 15,540

[22] Filed: Feb. 26, 1979

[51] Int. Cl.$^3$ ...................... A61K 37/00; A61K 35/00
[52] U.S. Cl. ..................................... 424/93; 424/115
[58] Field of Search .................................. 424/93, 115

Primary Examiner—Jerome D. Goldberg
Attorney, Agent, or Firm—M. Howard Silverstein; William E. Scott; David G. McConnell

[57] ABSTRACT

This invention relates to a method of biologically controlling plant diseases caused by sclerotia of sporidesmium susceptible plant pathogenic fungi.

1 Claim, No Drawings

BIOLOGICAL CONTROL SYSTEM

BACKGROUND OF THE INVENTION

1. Field of the Invention

This invention relates to a system for the biological control of plant pathogenic fungi in soil and more particularly to the use of the mycoparasite, *Sporidesmium sclerotivorum*, to control and destroy or eradicate the sclerotia of plant pathogenic fungi susceptible to Sporidesmium such as those of the genus Sclerotinia and *Sclerotium cepivorum*. The invention also relates to a novel method of producing the mycoparasite, *Sporidesmium sclerotivorum*.

2. Description of the Prior Art

Although the concept of biological control of plant disease microorganisms has been known for a number of years, there is no known relevant art regarding the mycoparasite, *Sporidesmium sclerotivorum*, because it has only recently been discovered.

A subculture of this mycoparasite can be obtained from the permanent collection of the Northern Regional Research Center, Science and Education Administration, U.S. Department of Agriculture, Peoria, Ill., U.S.A., 61604. Its Accession No. in this repository is NRRL 11437. As of the filing date of this application, progeny of the subject strain will be made available to anyone who requests the same. A taxonomic description of the mycoparasite is found in Mycotaxon 7, 275–282, 1978, which is herein incorporated by reference.

*Coniothyrium minitans* is a well known mycoparasite of Sclerotinia spp. and Sclerotium spp. and under controlled conditions has shown promising results in reducing the inoculum potential of these fungi. However, a field trial in soil naturally infested with *S. sclerotiorum* was only partially successful.

BRIEF SUMMARY OF THE INVENTION

An object of this invention is to provide a simple, economically sound, non-polluting means of controlling plant disease.

Another object is to provide a means of increasing yields of agricultural products by controlling and eradicating soil-borne plant pathogenic fungi.

A further object is to provide means of increasing plant health and yields of agricultural products while reducing or eliminating the use of chemicals for disease control.

A still further object is to provide a means of biologically controlling the sclerotia of the plant pathogenic fungi of the genus Sclerotinia and *Sclerotium cepivorum*, the causative agents of lettuce drop, bean white mold, peanut blight, onion white rot, and other serious plant diseases of food crops and other plants such as sunflower, clover and alfalfa.

Still another object is to provide a novel method of producing the mycoparasite, *Sporidesmium sclerotivorum*.

According to this invention the above objects are accomplished by a novel method of producing the mycoparasite, *Sporidesmium sclerotivorum*, wherein a sterilized culture medium that will support the growth of sclerotial producing fungus is inoculated with a species of fungus susceptible to Sporidesmium, the inoculated medium incubated at a temperature and for length of time effective for the production of sclerotia, and the sclerotia collected and added to fine quartz sand or other inert media. A culture of *S. sclerotivorum* is then added to and thoroughly mixed with the sand-sclerotia mixture and incubated at a temperature and for a length of time effective for the growth and production of Sporidesmium.

The above objects are further accomplished by a method wherein an effective sclerotia destroying amount of an inoculum of the so-produced mycoparasite, *Sporidesmium sclerotivorum*, is added to and mixed with soil to at least that depth at which Sporidesmium susceptible sclerotia reside and allowed to develop in the soil for that length of time required for the Sporidesmium to effectively infect, consume and destroy at least 90% of the Sporidesmium susceptible pathogenic sclerotia in the soil.

DESCRIPTION OF THE INVENTION

The control of soilborne plant diseases is the greatest unresolved problem of plant pathology. Conventional breeding for resistance has provided effective relief from very few of these diseases. Crop rotations, although sometimes effective, are becoming less and less practical under today's economic pressures. The use of chemical pesticides is frequently economically impractical or ecologically unacceptable. Therefore, finding how to produce the recently discovered mycoparasite, *Sporidesmium sclerotivorum*, and how to use it to achieve biological control of plant disease is a very important discovery.

The recently discovered mycoparasite of plant pathogens such as the genus Sclerotinia and *Sclerotium cepivorum*, the causative agents of lettuce drop, bean white mold, peanut blight, onion white rot, and other serious plant diseases of food crops and other plants, destructively infects living sclerotia of the plant pathogens in natural soils in which it is introduced. The genus Sclerotinia includes three species: *S. minor*, *S. trifolium*, and *S. sclerotiorum*. Complete destruction of sclerotia by the mycoparasite, *Sporidesmium sclerotivorum*, can be effected within ten weeks. The mycoparasite has the unusual ability to grow through soil from the host sclerotium to another and produce great numbers of conidia throughout the soil.

Certain plant pathogenic fungi as, for example, the Sclerotinia species and *Sclerotium cepivorum* cause severe economic losses throughout the United States and other countries on many vegetable crops including beans, lettuce, celery, potatoes, and tomatoes; on several oil crops including mint, peanut, and sunflower; and on forage legumes including clover and alfalfa. For most of these diseases there are no satisfactory chemical control measures available, nor are there genetically resistant plant varieties.

Sclerotia are the principal survival structures of certain soilborne plant pathogenic fungi and constitute an important link in the epidemiology of plant diseases caused by several plant pathogens. These hard, resistant fungal structures survive desiccation in soil and can remain viable for years and act directly as sources of infection.

We attempted to culture *Sporidesmium sclerotivorum* on ordinary culture media with no success. After much experimentation and many failures, we found that a medium prepared from comminuted sclerotia of *S. minor* in sterile water agar permitted germination of conidia of the fungus. Later, we obtained an axenic culture of the fungus from such a single germinated conidium. We tried to culture the isolate on many different potential substrates, such as sugars, amino acids, and vitamins, as well as on complex media that support the growth of many fastidious microorganisms, but were not successful. However, we did achieve continued growth of the isolate on media prepared from sclerotia of *S. minor* and on living sclerotia. Supplementation of sclerotial agar with a variety of extracts and compounds had either no observable effect or in some cases inhibited germination. The addition of the following substances in 0.1% concentrations to sclerotial agar did not further stimulate germination or growth: glucose, sucrose, trehalose, mannitol, chitin, melanin, calcium lignosulfonate, and yeast extract. Sterile soil extract (10 g loam stirred vigorously in distilled water for 1 hour, filtered, and sterilized by membrane filtration or by autoclaving) added to sclerotial agar before solidification also did not stimulate growth greater than that occurring on sclerotial agar alone.

Other media which did not support either germination or growth included the following: water agar, potato dextrose agar, 0.1 and 1% yeast extract, V-8 juice agar, and trypticasesoy agar. Autoclaved culture filtrates of *S. minor* grown for 14 days from potato dextrose broth (PDB), and moist autoclaved soil from which the isolate was originally obtained, also did not permit germination or growth. It did grow, but very poorly, on corn meal agar.

We discovered that unlike other mycoparasites such as *Coniothyrium minitans* Camp., *S. sclerotivorum* invades only the sclerotia of Sclerotinia species and *Sclerotium cepivorum* and not the hyphae. We prepared agar media from comminuted washed hyphae mats containing sclerotia harvested from PDB cultures of *S. minor* 14 days old and found that it supported germination and growth of macroconidia and growth of the isolate. However, on a similar medium prepared from mats 7 days old which had not yet formed sclerotia, we obtained neither germination nor growth. This discovery indicates that sclerotia but not Sclerotinia hyphae contain an essential growth promoting substance for *S. sclerotivorum.* We found further evidence of this when we accomplished a gnotobiotic culture of *S. sclerotivorum* in vivo by the addition of small pieces of sclerotial agar bearing hyphae and conidia of the isolate to aseptically washed mycelial mats of *S. minor* with sclerotia from 4-week-old PDB cultures. After 3 weeks at 25° C. many of the sclerotia were obviously infected and hyphae of the mycoparasite had spread throughout the culture forming new, typical macroconidia. The Sclerotinia hyphae were not invaded by *S. sclerotivorum.*

We found that when we mixed sclerotia of *S. minor* into a natural soil and then artificially infested the mixture with a sand-sclerotia culture of *Sporidesmium sclerotivorum,* the sclerotia were rapidly infected by the mycoparasite. Survival of the sclerotia, as measured by their recovery on soil sieves, dropped dramatically after five weeks and almost to zero in ten weeks. The numbers of sclerotia in control soil to which the mycoparasite had not been added remained at about the original level. We obtained equivalent results when we repeated the experiment in different natural soils including soils in which the mycoparasite was introduced, that is, soils in which it was not a natural inhabitant.

In our search for ways to grow and utilize the newly discovered mycoparasite as a biocontrol agent for sclerotial plant pathogens we found that *Sporidesmium sclerotivorum* has several distinctive qualities that make it a potentially-important biocontrol agent for sclerotial plant pathogens. Development of *S. sclerotivorum* is favored by living, rather than dead, sclerotia. The mycoparasite convincingly attacks sclerotia in natural soil in which it is introduced, as well as in soils in which it is a natural inhabitant. It spreads over and through soil from one sclerotium to another producing abundant conidia along its hyphae which serve as new infective units for further mycoparasitism of sclerotia. It forms thick-walled chlamydospores, which may function as propagules for long-term survival. These distinctive characteristics are lacking in most other mycoparasites of sclerotial fungi.

The method of propagation of Sporidesmium and the method of its use differs significantly from previously known concepts of mycoparasite-biological control systems. Sporidesmium is cultured on living sclerotia of the plant pathogen for which biological control is sought. Other mycoparasites proposed for biological control of Sclerotinia and Sclerotium species are cultivated on sterilized grain, molasses or other sterilized organic material. Sporidesmium is grown in moist quartz sand or other inert media. It does not derive any nutrients from the media; all of its nutrients are derived from sclerotia which is added to the sand. Other fungi suggested for biological control derive nutrients from the grain or other organic media on which they are grown.

The novelty of the present invention is attested to by the fact that there is only one antifungal biological control agent registered with the Environmental Protection Agency in the United States. This biological control system concerns the inoculation of pine stumps with *Peniophora gigantea* against infections of *Fomes annosus,* Ann. Appl. Biol. 52, 63–77, 1963.

The use of the living host material (sclerotia) as the substrate for propagation and dissemination of the mycoparasite is completely new and has several advantages over other methods:

(a) It is not necessary to sterilize or maintain sterility in the mixtures during propagation. Living sclerotia have a natural resistance to invasion by most common soil microorganisms; thus, only certain mycoparasites, such as Sporidesmium, can invade the sclerotia and thereby propagate themselves without hinderance from contaminating microorganisms. On the other hand, sterilized organic materials such as cereal grains are subject to attack by a great many common bacteria and fungi, which may interfere in the cultivation of the mycoparasite unless special precautions are taken to exclude them.

(b) The use of living host sclerotia in the propagating medium insures that the mycoparasitic behavior of the fungus is maintained, since it can obtain nutrients for growth only from the host. In contrast, mycoparasites propagated on sterilized organic matter may possibly lose or decrease their parasitic activity.

(c) The delivery of the mycoparasite in such infected sclerotia mixtures to soil aids in the infection of sclerotia naturally present in the soil by serving as food bases from which the mycoparasite can expand. The presence of these specialized food bases (infected sclerotia) coupled with the distinctive, spreading behavior of Sporidesmium in soil is beneficial in hastening the mycoparasitism and biological control.

The invention is illustrated by the following examples:

Preparation of Sporidesmium Inoculum

In general, the method consists of culturing *Sporidesmium sclerotivorum* in living sclerotia of a species of fungus which is susceptible to Sporidesmium as, for example, the Sclerotinia species and *Sclerotium cepivorum* in moist quartz sand or in other inert supporting media, at a temperature of 15° to 25° C. The preferred method of culture at present is the following:

(a) Sclerotia of *S. minor* are first cultured on moist, sterilized animal-feed oats in sterile glass containers. Oats and water in the ratio of 50:60 by weight are sterilized by autoclaving at 121° C. for 30 minutes. An inoculum of *S. minor* is introduced aseptically into the oats and the preparation is then incubated at room temperature (20°–25° C.) for 4 weeks or longer. The medium for producing the sclerotia is not critical, a variety of materials may be used.

(b) Sclerotia are separated from the oats and collected by passing the mixture through appropriate-sized soil sieves, preferably with the aid of running water.

(c) Collected sclerotia are added to fine quartz sand at the rate of 1% to 2% by weight and water is added to achieve a favorable moisture level (about 13% by weight with fine grained quartz sand). Not essential, but preferred because it improves the growing medium somewhat, is the addition of powdered calcium carbonate, 0.01 to 0.7% by weight, to maintain a favorable pH and to ensure longer viability of the mycoparasite.

(d) *Sporidesmium sclerotivorum* is added as a seed inoculum to the sclerotia-sand mixture in any suitable container such as a beaker or a plastic flat, from either a pure culture of mycoparasite (spore suspension) or preferably by the addition of about 1% (larger amounts may also be used) by weight of a sand-sclerotia culture of Sporidesmium. The mixture is thoroughly mixed and incubated at room temperature (20°–25° C.) for 7 weeks or longer.

(e) *Sporidesmium sclerotivorum* grows and develops in the mixture by invading sclerotia of the plant pathogen and spreads by extension of hyphae over the sand particles, producing a great many spores or macroconidia over the surface, and in the depths of the sand. The numbers of the macroconidia, each of which is a potential sclerotium-infecting unit, can be quantitated by making counts of representative samples of the mixture by conventional microbiological microscope procedures. These mixtures usually develop 100,000 to 500,000 macroconidia per gram of sand-sclerotia material.

Use of Sporidesmium in the Biological Control of Plant Pathogens and Plant Disease In general, the procedure consists of adding an inoculum of Sporidesmium sclerotivorum furnished in a sand-sclerotial mixture to soil which contains sclerotia of the plant pathogen which, for laboratory experiments, is artificially added to field soil containing sclerotia of the plant pathogen produced under natural conditions. The material is mixed into the soil and the mycoparasitism is permitted to develop in fallow soil for at least 10 weeks, preferably at beneficial soil temperatures of 15°–25° C., a soil pH of 5.0 to 8.0 and moisture levels of 70% of field capacity or higher. Under the conditions we used in our field experiments we obtained good results by allowing the mycoparasite to develop in the soil for 20 weeks. However, there is no reason why this time period cannot be shortened by altering the conditions. Macroconidia of Sporidesmium germinate in the soil immediately adjacent to individual sclerotia, the germ tubes elongate and, by mechanisms unknown, penetrate the sclerotia. Sclerotia thus infected, gradually become consumed by the mycoparasite and eventually become completely destroyed. The beneficial result of this destructive process is the decrease, or elimination, of sclerotia in the soil which can cause plant disease.

Two examples of the use of Sporidesmium are given below:

LABORATORY EXPERIMENT

A natural slit loam was moistened to 70% of field capacity and artificially infested with sclerotia of *Sclerotinia minor* at the rate of 1% by weight and added to beakers in 150 g quantities. Four replicate beakers of the soil were treated with Sporidesmium by the addition of 1.5 g of moist, sand-sclerotia cultures of the mycoparasite followed by mixing. Four replicate beakers of the soil were kept as controls for comparison. Soil temperature and pH were about 25° C. and 6:0, respectively. At weekly intervals, 5 gram samples of the soils were removed and the sclerotia from the samples were screened out and counted. The retrieved sclerotia were placed on moist filter paper in petri dishes for 2 weeks at 25° C. to determine the numbers which had become infected by the mycoparasite. In five weeks, 100% of the sclerotia were infected and by ten weeks, survival of the sclerotia was reduced almost to zero. Another experiment with an entirely different soil type produced practically indentical results.

FIELD EXPERIMENT

Field plots, 10 feet square, were established at Beltsville, Maryland, in a field that contained a natural population of the lettuce drop pathogen, *Sclerotinia minor.* The numbers of sclerotia in the plots were determined to vary from 12 to 37 sclerotia/100 g of soil.

Five replicate plots each were treated with *Sporidesmium sclerotivorum* by the addition of weighed portions of sand-sclerotia cultures to the soil surface. The soil and Sporidesmium inoculum were rototilled to a depth of six inches. The pH of the soil was about 6.0 and the ambient atmospheric temperature ranged from about 10° C. to about 30° C. The experiment was started in late spring of 1978 and the results in Table 1 were obtained the following summer. At each sampling period of four weeks, the plots were rototilled and soil samples were taken for assay. The numbers of sclerotia per 100 g of soil were determined and expressed as the percentage of the numbers that were present at the beginning of the experiment.

The rate of application and the results of the experiment are shown in Table 1. The results indicate that the two highest treatments, 2,000 and 20,000 lbs/acre of the Sporidesmium-sand mixture were responsible for a significant reduction in the numbers of sclerotia after 20 weeks. The results of further sampling at 24 weeks are also shown in Table 1. The population of sclerotia per 100 g of soil prior to addition of Sporidesmium is shown at zero weeks in Table 1.

TABLE 1.

Treatments and results of biological control field test using *Sporidesmium sclerotivorum* to reduce the population of *Sclerotinia minor*.

| Rate of Sporidesmium mixture added to field plots (lbs/acre) | Population of S. minor (Sclerotia/100 g) | | | Percent Reduction of S. minor | |
|---|---|---|---|---|---|
| | zero weeks | 20 weeks | 24 weeks | 20 weeks | 24 weeks |
| 0 | 22.2 | 13.8 | 14.6 | 37.8 | 34.2 |
| 20 | 20.0 | 12.2 | 14.8 | 39.0 | 26.0 |
| 200 | 16.2 | 9.8 | 12.2 | 39.5 | 24.7 |
| 2,000 | 24.0 | 6.4 | 5.2 | 73.3 | 78.3 |
| 20,000 | 24.0 | 1.8 | 1.4 | 92.5 | 94.2 |

We claim:

1. A method of biologically controlling plant diseases caused by sclerotia of Sporidesmium susceptible plant pathogenic fungi, comprising:

(a) producing the mycoparasite *Sporidesmium sclerotivorum* by adding an inoculum of *Sporidesmium sclerotivorum* NRRL 11437 to an inert culture medium containing living sclerotia of a species of fungi susceptible to the Sporidesmium and culturing said mycoparasite at about from 15° to about 25° C. until about 100,000 to 500,000 macroconidia per gram of said inert culture medium are produced;

(b) adding to soil containing Sporidesmium susceptible plant pathogenic fungi, an inoculum of *Sporidesmium sclerotivorum* produced in step (a), said inoculum being added at the rate of about from 2000 to about 20,000 pounds per acre and said soil having a pH of about from 5.0 to about 8.0, a moisture level of about 70%, and a temperature range of from about 10° to about 30° C.;

(c) mixing the inoculum into the soil to at least that depth at which the aforesaid sclerotia reside; and (d) allowing the Sporidesmium to develop in the soil until it infects, consumes and destroys at least 90% of said sclerotia.

* * * * *